United States Patent [19]

Isobe et al.

[11] Patent Number: 5,603,945

[45] Date of Patent: Feb. 18, 1997

[54] THERAPEUTIC/PROPHYLACTIC AGENTS AND METHOD OF TREATING FOR URINARY CALCULOSIS IN PETS

[75] Inventors: Yoshio Isobe, Suginami-ku; Toshio Ito, Suita; Norio Kogure, Bunkyo-ku; Hideaki Narita, Suginami-ku; Norio Hanazawa, Minato-ku; Kiichi Kanayama, Ebina, all of Japan

[73] Assignee: Takeda Chemical Industries, Ltd., Osaka, Japan

[21] Appl. No.: 197,591

[22] Filed: Feb. 17, 1994

[30] Foreign Application Priority Data

Feb. 19, 1993 [JP] Japan ..................... 5-054944

[51] Int. Cl.$^6$ ............................. A23K 1/165; A23K 1/17
[52] U.S. Cl. ......................................... 424/442; 424/439
[58] Field of Search ................................. 424/439, 442; 426/805; 514/557, 784

[56] References Cited

U.S. PATENT DOCUMENTS

| | | | |
|---|---|---|---|
| 4,362,710 | 12/1982 | Watanabe | 424/14 |
| 4,412,986 | 11/1983 | Kawata et al. | 424/80 |
| 4,424,234 | 1/1984 | Alderson et al. | 424/317 |

OTHER PUBLICATIONS

G. F. Taton et al., "Evaluation of ammonium chloride as a urinary acidifier in the cat", JAVMA, vol. 184, No. 4, Feb. 15, 1984, pp. 433–436.

L. D. Lewis et al., "Feline urologic syndrome: causes and clinical management", Veterinary Medicine, Companion Animals/Cats, Mar. 1984, pp. 323–337.

K. C. Bovée et al., "Recurrence of Feline Urethal Obstruction", JAVMA, vol. 174, No. 1, Jan. 1, 1979, pp. 93–96.

W. E. Lloyd et al., "Effects of orally administered ammonium chloride and methionine on feline urinary acidity", Veterinary Medicine, Companion Animals / Cats, Jun. 1984, pp. 773–778.

L. J. Rich et al., "Feline Urethral Obstruction: Mineral Aspects", Am. J. Vet. Res., vol. 29, No. 11, pp. 2149–2156, Nov. 1968.

D. R. Finco et al., "Characterization and Treatment of Water, Electrolyte, and Acid–Base Imbalances of Induced Urethral Obstruction in the Cat", Am. J. Vet. Res., vol. 38, No. 6, pp. 823–830, Jun. 1977.

G. F. Taton et al., "Urinary acidification in the prevention and treatment of feline struvite urolithiasis", JAVMA, vol. 184, No. 4, Feb. 15, 1984, pp. 437–443.

J. S. Reif et al., "Feline Urethral Obstruction: A Case–Control Study", JAVMA, vol. 170, No. 11, Jun. 1, 1977, pp. 1320–1324.

C. F. Burrows et al., "Characterization and Treatment of Acid–Base and Renal Defects Due to Urethral Obstruction in Cats", Javma, vol. 172, No. 7, Apr. 1, 1978, pp. 801–805.

Y. Maede et al., "Methionine–Induced Hemolytic Anema with Methemoglobinemia and Heinz Body Formation in Erythrocytes in Cats", vol. 38, pp. 568–571, 1985.

J. R. Burns et al., "Solubility product of magnesium ammonium phosphate hexahydrate at various temperatures", pp. 426–428.

C. A. Osborne et al., "Feline Cystitis, Urethitis, Urethral Obstructional Syndrome", Part I, Etiopathogenesis and Clinical Manifestations, Modern Veterinary Practice, Mar. 1978, pp. 173–180.

C. A. Osborne et al., "Feline Cystitis, Urethitis, Urethral Obstructional Syndrome", Part II, Therapy of Disorders of the Upper and Lower Urinary Tract, May 1978, pp. 349–357.

J. L. Parks, "Complications of Urogenital Tract Surgery", pp. 391–394.

J. E. Brown et al., "Ammonium Chloride/Methionine Toxicity in Kittens", Feline Pratice —Toxicology, vol. 14, No. 2, Mar.–Apr. 1984, pp. 16–19.

D. F. Senior et al., "Effectiveness of Ammonium Chloride as a Urinary Acidifier in Cats Fed a Popular Brand of Canned Cat Food", Feline Practice, Nov.–Dec. 1986, vol. 16, No. 6, pp. 24–27.

C. A. Osborne, et al., "Feline Cystitis, Urethritis, Urethral Obstruction Syndrome, Adverse Drug Reactions; Client Education", Sep. 1978, pp. 668–673.

C. A. Osborne et al., "Feline Cystitis, Urethritis, Urethral Obstruction Syndrome, Prophylaxis", Jul. 1978, pp. 513–519.

Primary Examiner—Thurman K. Page
Assistant Examiner—Sharon Howard
Attorney, Agent, or Firm—Foley & Lardner

[57] ABSTRACT

A preparation or a pet food comprising an edible carboxylic acid, edible hydroxycarboxylic acid such as fumaric acid or a salt thereof is administered or fed to a pet. The content of the edible organic acid or a salt thereof is, in terms of the edible organic acid, about 0.1 to 99.9% by weight for the preparation such as a solid preparation and about 0.01 to 10% by weight for the pet food such as a dry food. The dose of the edible organic acid or a salt thereof is, in terms of the edible organic acid, about 5 to 500 mg/day/kg of body weight. The preparation and pet food have an improved palatability and safety in comparison with a conventional urine-acidifying agent, thus the administration or feeding of said preparation or pet food prevent or treat urinary calculosis in a pet even in a small amount.

15 Claims, No Drawings

THERAPEUTIC/PROPHYLACTIC AGENTS AND METHOD OF TREATING FOR URINARY CALCULOSIS IN PETS

FIELD OF THE INVENTION

The present invention relates to a therapeutic and/or prophylactic agent useful for prophylaxis and therapy of urinary calculosis in a pet (for example, a small animal such as a dog and cat), and a method of treating and/or preventing such a disease.

BACKGROUND OF THE INVENTION

The formation of struvite (ammonium magnesium phosphate; $MgNH_4PO_4$) urinary calculus, which occurs most frequently among urinary calculuses or uroliths of dogs and cats, is mainly caused by an increase in urine pH.

The struvite urinary calculosis or urolithiasis in cats occupies about 88% of urinary calculosis, and said calculus is composed of struvite as ammonium magnesium phosphate hexahydrate, a small amount of calcium apatite, ammonium urate and uric acid. The struvite urinary calculosis (urolithiasis) is principally caused by saturation of the concentration of ammonium magnesium phosphate in urine, depending on species of a diet to be fed, a shortage of water supply, a lack of exercise or others, and is further attracted by a urinary infection of a urease-producing microorganism.

With regard to methods for nutritionally preventing urinary calculus, there have been reported (1) a technique increasing the amount of urination by means of raising the water intake, (2) a technique wherein a diet to be supplied is modified or changed gradually from a wet food to a dry food (a solid dry food), (3) a technique which comprises restricting the intakes of magnesium components and phosphorus components in a diet and increasing the contents of sodium salts in the diet, (4) a technique where a urine-acidifying agent is administered for acidification of urine, and others.

The technique using the urine-acidifying agent makes a profit from the fact that the urine pH of 6.6 or more frequently causes the struvite urinary calculus and, conversely, the urine pH of 6.5 or less reduces the formation of the calculus.

The administration of the urine-acidifying agent is, among these techniques, effective for maintaining the urine acidic so as to dissolve the struvite urinary calculus as well as for preventing the formation of the urinary calculus.

As the urine-acidifying agent, there have been reported, for example, DL-methionine, ammonium chloride, ascorbic acid (vitamin C), ethylenediamine dihydrochloride, sodium hydrogenphosphate and the like.

The use of these urine-acidifying agents, however, has disadvantages that it may cause a disorder depending on the dose of the urine-acidifying agents. For example, it has been reported that an excessive intake of methionine is harmful and that administration of a urine-acidifying agent, especially DL-methionine, ammonium chloride, is not recommended since it has a plural of disadvantages such as a poor palatability, thus causing dysorexia or vomition, enhancing intoxication or growth retardation [Clinical Nutrition in Small Animals III, Lon D. Lewis et al., published by Mark Morris Research Center, Oct. 31, 1989, pp. 9–41 to pp. 9–46, and R. Wolter's Nutrition in Cats and Dogs, R. Wolter, published by Nihon Rinsho-sha, Mar. 20, 1991, pp. 223–232.].

The struvite urinary calculosis among whole urinary calculosis in dogs occurs in a proportion of about 80 to 97% in female and immature male dogs, and about 50 to 75% in matured dogs, hence the occurrence thereof takes overwhelmingly major as compared with other urinary calculosis such as urinary calculus caused by calcium oxalate, ammonium urate, cystine, or a salt of silicic acid. It has been known that the urinary calculosis may also be caused by suppression of urination, a shortage of exercise, obesity, gonadectomy and other factors. Further, the formation of the struvite urinary calculus is liable to be promoted by supplying a dog with a food containing a high concentration of magnesium, salts of phosphoric acid and calcium components, and such formation is also induced by infection of a urease-producing microorganism.

There has been known as techniques for preventing or treating the urinary calculosis in dogs that (5) a technique wherein a urinary infectious disease is radically cured or controlled with the use of a suitable antibiotic; (6) a technique which comprises increasing the intake of sodium chloride or saline for promoting urination; (7) a technique where a diet for dissolving calculus is supplied; (8) a technique which comprises administering a urease-inhibitor such as acetohydroxamic acid to a dog of urinary infectious disease caused by a urease-producing microorganism; (9) a technique which comprises administering the urine-acidifying agent, and others.

The administration of acetohydroxamic acid in a dose of 25 to 100 mg/kg of body weight per day is effective on suppressing the urease activity in urine, lowering the urine pH, reducing crystalline urine, and, still more, dissolving the urinary calculus. Said administration, however, may bring about hemolytic anemia, and in a certain species of dog, show a teratogenicity. Further, it has been reported that the use of the urine-acidifying agent is not also recommended similarly as mentioned above in cats [Clinical Nutrition in Small Animals III, Lon D. Lewis et al., published by Mark Morris Research Center, Oct. 31, 1989, pp. 10–3 to pp. 10–40, and R. Wolter's Nutrition in Cats and Dogs, R. Wolter, published by Nihon Rinsho-sha, Mar. 20, 1991, pp. 237–245].

SUMMARY OF THE INVENTION

Accordingly, it is an object of the present invention to provide a therapeutic and/or prophylactic agent and a pet food for urinary calculosis in a pet, which can treat or prevent the urinary calculosis in a pet, for example, a small animal such as a cat or dog, with an improved palatability and without side effects.

It is another object of the invention to provide a therapeutic and/or prophylactic agent and a pet food for urinary calculosis in a pet, which have a high palatability and a prolonged residence time in a body and can effectively treat, cure or prevent the urinary calculosis in a pet even in a small amount.

Still another object of the present invention is to provide a therapeutic and/or prophylactic agent and a pet food capable of reducing the urine pH efficiently, and can effectively treat, cure or prevent the urinary calculosis in a pet.

A further object of the invention is to provide a method for treating or preventing the urinary calculosis in a pet efficaciously.

After much research with the fact of an edible organic acid having a high safety, the inventors of the present invention found that the therapy and prophylaxis of the urinary calculosis can be successfully achieved without any side effect by administering or supplying a pet with a preparation or a pet food comprising a certain edible organic acid or a salt thereof, and that such a preparation or a pet food has a good palatability. The present invention has been accomplished based on the above findings.

Thus, a therapeutic and/or prophylactic agent and a pet food of the present invention comprise an edible carboxylic acid, edible hydroxycarboxylic acid or a salt thereof.

The edible carboxylic acid and edible hydroxycarboxylic acid may be selected from a variety of compounds having a carboxylic group, for example, an aliphatic monocarboxylic acid, an aromatic monocarboxylic acid, an aliphatic polycarboxylic acid, an aliphatic hydroxycarboxylic acid, an aromatic hydroxycarboxylic acid or others. The edible carboxylic acid, edible hydroxycarboxylic acid or a salt thereof may be solid at room temperature, or used in a powdery or granular form.

The therapeutic and/or prophylactic agent for the urinary calculosis in a pet may be composed of, for example, a solid preparation, and such a solid preparation may further comprise, for instance, an excipient, a binder and a sweetener. The solid preparation may be a coated preparation.

The pet food may be a dry food, a semidry food or a wet food, and may contain, in the powdery or granular form, the edible carboxylic acid, edible hydroxycarboxylic acid or a salt thereof which may be solid at room temperature.

According to the method of the present invention, the urinary calculosis in a pet is treated or cured by administering, feeding or supplying a pet with an edible carboxylic acid, edible hydroxycarboxylic acid or a salt thereof. The dose of said edible carboxylic acid, edible hydroxycarboxylic acid or a salt thereof may be selected from an adequate range according to conditions such as the urine pH.

DETAILED DESCRIPTION OF THE PREFERRED EMBODIMENT OF THE INVENTION

In this specification, the edible carboxylic acid and edible hydroxycarboxylic acid are, unless otherwise defined, generally referred to as "edible organic acid" or "organic acid". Regarding the grain or particle diameter or size, the term "not finer than 300 mesh" means "a diameter or size of a particle which does not pass through a 300-mesh sieve and remains on the sieve".

The edible organic acid mentioned above is not critical as far as being a carboxylic acid and edible hydroxycarboxylic acid having a high safety, and can be selected from compounds approved as food additives. The edible organic acid includes, for example, a monocarboxylic acid (e.g. an aliphatic monocarboxylic acid including an aliphatic saturated monocarboxylic acid such as acetic acid, propionic acid and butyric acid, and an aliphatic unsaturated monocarboxylic acid such as sorbic acid; and an aromatic monocarboxylic acid such as benzoic acid), an aliphatic polycarboxylic acid (for instance, an aliphatic saturated polycarboxylic acid including a dicarboxylic acid such as oxalic acid, malonic acid, succinic acid, glutaric acid and adipic acid; and an aliphatic unsaturated polycarboxylic acid including a dicarboxylic acid such as fumaric acid) and a hydroxycarboxylic acid (for example, an aliphatic hydroxycarboxylic acid such as lactic acid, malic acid, tartaric acid, citric acid and gluconic acid; and an aromatic hydroxycarboxylic acid such as p-hydroxybenzoic acid). These edible organic acid can be used singly or in combination.

Examples of the preferred edible organic acid include an aliphatic monocarboxylic acid, an aliphatic polycarboxylic acid and hydroxycarboxylic acid, more preferably an aliphatic unsaturated polycarboxylic acid and an aliphatic hydroxycarboxylic acid.

The edible organic acid may be used in the form of a salt. As the salt of the edible organic acid, there may be mentioned, for example, a salt with an alkali metal, e.g. potassium, sodium, etc., and ammonium. When an edible organic acid having two or more carboxyl groups is employed, the salt formed with at least one of the carboxyl groups of the edible organic acid is also included. The organic acid and any of such salts thereof may be used in combination. The edible organic acid or a salt thereof having an asymmetric carbon may be an optically active substance, for instance, a D-, L-, or DL-form, or may be a racemic form or meso form.

The therapeutic and/or prophylactic agent and the pet food comprising such an edible organic acid or a salt thereof are characterized by having an improved safety and palatability in comparison with a conventional urine-acidifying agent without causing dysorexia or vomition and is effective in a small amount.

The edible organic acid and a salt thereof may be used in a liquid form, but an edible organic acid or a salt thereof which is solid at room temperature, e.g. at about 10° to 40° C., is preferable to improve the palatability and to prolong the residence time of the organic acid in the body, and such a preferred organic acid or its salt may have, for instance, a melting point of about 45° to 300° C. and preferably about 100° to 300° C. The organic acid in a solid form at room temperature includes, for example, an aliphatic unsaturated monocarboxylic acid, an aromatic monocarboxylic acid, a polycarboxylic acid and a hydroxycarboxylic acid. An organic acid in a liquid form at room temperature, for instance, an aliphatic saturated monocarboxylic acid such as acetic acid, or lactic acid are preferable to be employed as a salt being solid at room temperature such as an ammonium salt.

Preferred examples of the edible organic acid include a poorly or sparingly soluble organic acid (e.g. an organic acid having a less or poor solubility in water), for example, an organic acid having a solubility, in 100 g of water at 25° C., of 20 g or less, preferably about 0.1 to 10 g and more preferably about 0.1 to 5 g. As the edible organic acid having a lesser or sparse solubility in water, there may be mentioned, for example, an aliphatic unsaturated monocarboxylic acid such as sorbic acid, and an aliphatic polycarboxylic acid having about 2 to 6 carbon atoms such as oxalic acid, malonic acid, succinic acid, glutaric acid, adipic acid and fumaric acid. The aliphatic saturated polycarboxylic acid having an even number of carbon atoms, and fumaric acid have a specifically poor or sparse solubility in water among others. Use of the edible organic acid having a lesser solubility can prolong the residence time (retention time) of the organic acid in a body and improve the therapeutic effects for the urinary calculosis.

Aliphatic polycarboxylic acids having about 2 to 6 carbon atoms, specifically fumaric acid, can advantageously be employed as the edible organic acid. Fumaric acid is one of the organic acids in the TCA cycle (tricarboxylic acid cycle), thus having an excellent safety and being low-priced. Additionally, since fumaric acid has a sparse or poor solubility in water, it can arrive to the inferior digestive tract and reside or retain in the body for a comparatively prolonged duration when administered to a small animal such as a dog and cat. Therefore, fumaric acid is useful in metabolic possesses for enhancing the exertion of hydrogen ion ($H^+$) to urine in a long duration of time so as to lower or decrease the urine pH and to acidify the urine and for dissolving the struvite calculus.

The organic acid or a salt thereof being solid at room temperature is frequently used in practice in a powdery or granular form. The mean grain or particle size or diameter of the powdery or granular organic acid or a salt thereof may be, for example, not finer than about 300 mesh, preferably about 250 to 5 mesh and more preferably about 200 to 10 mesh.

The therapeutic and/or prophylactic agent for urinary calculosis can be administered orally or non-orally and may be prepared in a suitable dosage form for oral administration such as a liquid preparation, e.g. emulsions, suspensions, syrups and the like, but practically preferred is a solid preparation such as tablets, fine granules, granules, powders, pills, capsules and dry syrups. The solid preparation as a tablet can be orally administered to a pet in a simple and easy manner. These solid preparations insure to prolong the residing period of the organic acid in the body, and are useful for the prophylaxis (prevention) and therapy (treatment) of urinary calculosis. Further, coated tablets are also appropriate to improve the palatability of the organic acid as well as the internal residence time.

The solid preparation for oral administration may be prepared by using conventional components. As the components of such preparation, there may be mentioned, for example, excipients such as lactose, powder sugar (sucrose), a sucrose ester, mannitol, corn starch, crystalline cellulose, talc, light silicic anhydride, magnesium carbonate, calcium carbonate, cyclodextrin etc.; binders such as hydroxypropylcellulose, hydroxypropylmethylcellulose, alpha-starch, methylcellulose, carboxymethylcellulose, polyvinylpyrrolidone, pullulan, dextrin, gum arabic, etc.; disintegrators such as carboxymethylcellulose calcium, low-substituted hydroxypropylcellulose, starches, etc.; surfactants including anionic surfactants such as sodium alkylsulfates, and non-ionic surfactants such as polyoxyethylene-sorbitan fatty acid esters, polyoxyethylene-fatty acid esters, etc.; colorants such as titanium oxide, iron red oxide and tar pigment; perfumes, vitamins, amino acids, minerals and dairy products such as cheese; and so on.

At least the excipient can frequently be used as the additive, and the binder may further advantageously be employed.

When used in combination with a sweetener, the palatability of the preparation comprising the edible organic acid or a salt thereof can be improved. Example of the sweetener includes a natural sweetener such as powder sugar, glucose, granulated sugar, fructose and lactose; a starch sugar such as isomerized sugar and reducing maltose starch syrup; a sugar-alcohol such as mannitol; an artificial sweetener such as aspartame. These sweeteners can be employed independently or in combination. The amount of the sweetener to be added is, for example, about 0.05 to 50% by weight and preferably about 0.1 to 50% by weight, respectively based on the weight of the preparation.

The content of the edible organic acid or a salt thereof in the solid preparation can be selected from a wide range, and is, for example, about 0.1 to 99.9% by weight and preferably about 1 to 99% by weight in terms of the edible organic acid. When the solid preparation is a tablet, the proportion of the organic acid or a salt thereof per tablet is, in terms of the edible organic acid, frequently about 50 to 1,000 mg and preferably about 100 to 750 mg.

The solid preparation mentioned above can be produced by a conventional manner, for example, with the use of a tumbling granulator, a centrifugal-tumbling granulator, a stirring granulator, a fluidized-bed granulator, a tablet machine or the like.

Further, in order to mask the taste and improve the palatability, the edible organic acid or a salt thereof, especially the powdery or granular edible organic acid or a salt thereof, may be coated, and the solid preparation may be a sugar coated solid preparation (e.g. tablet) or a coated solid preparation (e.g. tablet) coated with a coating base. The examples of the coating base include gelatin, hydroxypropylmethylcellulose, ethylcellulose, hydroxymethylcellulose, hydroxypropylcellulose, low-substituted hydroxypropylcellulose, polyethylene glycol, polysorbate (e.g. tween 80, etc.), cellulose acetate phthalate, hydroxypropylmethylcellulose phthalate, acrylic acid copolymer, carboxymethylcellulose, carboxymethylethylcellulose, polyvinyl alcohol, polyvinyl acetal diethylamino acetate, shellac, waxes (for example, paraffin wax, carnauba wax, beeswax, montan wax, etc.), fatty acids and salts thereof, aliphatic higher alcohols, lipids, e.g. glycerol fatty acid esters such as castor oil and a hardened oil thereof (e.g. hardened castor oil, hardened beef oil, etc.) and dairy products such as cheese. At least one of these bases may be employed.

When coating the edible organic acid or a salt thereof, the coating amount of the coating base is, for example, about 1 to 80 parts by weight and preferably about 5 to 70 parts by weight, relative to 100 parts by weight of said edible organic acid or a salt thereof. For coating the solid preparation, the proportion of the base is, for example, about 1 to 50% by weight and preferably about 5 to 30% by weight based on the total weight of the preparation.

The coating procedure can be conducted in accordance with a conventional manner, for example, by spraying a coating composition including the base mentioned above. In such a case, the coating composition further comprising, for example, the binder can also be employed. The edible organic acid or a salt thereof may also be coated by, for instance, a technique comprising blending or mixing said organic acid or a salt thereof with a coating composition composed of said base and, if necessary, a suitable solvent, and granulating the mixture by e.g. spraying, or a technique spraying the floating organic acid or a salt thereof in powdery or granular form with the coating composition. Further, the edible organic acid or a salt thereof may be coated by, for example, blending or mixing the powdery or granular organic acid or a salt thereof with the coating composition comprising the melted or softened base as above at a temperature lower than the melting point of said acid or its salt, and granulating the mixture by spraying or the like. In such a coating procedure, a substance having a lower melting point wherein the melting point or softening point is lower than that of the organic acid or a salt thereof (for instance, a wax, a higher alcohol, a glycerol fatty acid ester, a hardened oil, etc.) can advantageously be used as the coating base.

The pet food (diet for a pet) may be in any form, for example, a mixed powder prepared by mixing or blending raw materials; a dry food in the form of e.g. meal (powdery), biscuits, pellets or the like; a semi-dry food such as a pet food containing about 10 to 50% by weight of water; and a wet food such as a canned food (for example, a pet food containing about 50 to 80% by weight of water). The dry food, more preferably the dry food comprising the powdery or granular edible organic acid or a salt thereof can advantageously be used to enhance the palatability.

The raw material of the pet food (the diet for a pet) can be selected from conventional components with reference to the species of the pet food. The components for the pet food include, for example, feeds of animal origin such as fish meal, fish meat, fishery products, fish solubles, cattle meat, meat scrap, meat-and-bone meal, blood meal, feather meal, silkworm cocoon oil meal, skimmed milk, whey, animal oils (e.g. beef oil, lard oil, bone oil, etc.), eggs, milks, brewers' yeast, torula yeast, etc.; cereals such as corn, milo, wheat, barley, rye, oat, wheat flour, unpolished rice, millet, soybean, soybean flour, cassava, etc.; starches such as alphastarch, starch, and the like; oil meals such as soybean meal, dehulled soybean meal, rapeseed oil meal, peanut oil meal, linseed oil meal, sesame oil meal, coconut oil meal, sunflower oil meal, safflower oil meal, palm kernel oil meal, kapok oil meal, etc.; brans such as rice bran, barley bran, wheat bran, etc.; factory byproducts such as gluten feed, gluten meal, starch meal, molasses, soy sauce byproducts, brewerys' byproducts, beat pulp, bagasse, soybean curd cake, malt sprouts, mandarin orange peels, mandarin orange juice cake, etc.; cellulosic materials such as alfalfa meal, timothy hay, straw, and the like; excipients, binders, disintegrators as mentioned above; sodium chloride or saline; sugars such as powder sugar; vitamins; amino acids; and minerals. These compositions can be used singly or in combination.

The pet food may further comprise, if necessary, a variety of additives such as an antibiotic, a preservative, an enzyme, an antifungal agent, an antioxidant, a colorant, a sweetener, a perfume and so on. The pet food may also be composed of the above-mentioned preparation comprising the edible organic acid or a salt thereof.

The content of the edible organic acid or a salt thereof in the pet food can be selected from the range where the palatability is not adversely affected and the urine pH is not lowered excessively, and is, for example, about 0.01 to 10% by weight, preferably about 0.05 to 5% by weight and more preferably about 0.1 to 2.5% by weight, in terms of the edible organic acid. In the semidry food or wet food, the amount of the organic acid or a salt thereof is frequently chosen from the range less than that of the dry food in order to prevent adverse effects on the palatability. Hence, the proportion of the edible organic acid or a salt thereof in the semidry food or wet food, is frequently, for instance, about 0.01 to 2.5% by weight and preferably about 0.1 to 1% by weight, in terms of the edible organic acid.

Oral administration or feeding (supplement) of the preparation or pet food as mentioned above can prevent the formation of urinary calculus and treat or cure urinary calculosis in a pet.

The dose of the therapeutic and/or prophylactic agent or the feeding amount of the pet food can be selected from the range depending on the symptoms or extent of the urinary calculosis, age, body weight and other factors, and is for instance, per kg of the body weight, about 5 to 500 mg/day, preferably about 10 to 400 mg/day and more preferably about 50 to 250 mg/day, respectively in terms of the edible organic acid. The therapeutic and/or prophylactic agent for urinary calculosis can be given regardless of whether it is before or after meals.

The edible organic acid or a salt thereof can be administered once a day, as well as in plural or several times daily, and in the later case, the urine pH can stably be maintained at a lower level. For treating (curing) or preventing urinary calculosis in a pet, an effective amount of the edible organic acid or a salt thereof may be often supplied or administered to sustain the urine pH at about 5.0 to 7.0 and preferably about 5.5 to 6.5.

The present invention can be applied to a variety of pets such as a dog, a cat, a mouse, a rat, a hamster, a rabbit, a monkey and the like, and preferably to a small animal such as a dog and a cat.

The following examples, comparative examples and preparation examples are intended to describe the present invention in further detail and should by no means be construed as limiting the scope of the invention.

EXAMPLES

Example 1

To a Japanese cat (1.5-years-old, male, 5 kg of body weight) wherein the amount of urination was small, and the urinary ketone form and the number of the leukocytes in urine were increased up to (±) and (++) respectively, a tablet (0.25 g) comprising 245 mg of fumaric acid per tablet was administered orally twice a day after meal, namely in the morning and in the evening, for 27 days. Thus, the results shown in Table 1 were obtained. In the Table, the amount of protein in urine was evaluated according to the following criteria:

−: normal
+/−: protein was detected slightly,
+: a little larger amount of protein was detected,
++: a large amount of protein was detected, and
+++: a remarkably large amount of protein was detected.

TABLE 1

|  | Urine pH | Specific gravity of urine | Protein in urine | Blood pH | Blood $pCO_2$ (mm Hg) | Blood $HCO_3^-$ (m mol/liter) |
| --- | --- | --- | --- | --- | --- | --- |
| Normal values | 6.5 or less | 1.020 to 1.040 |  | 7.10 to 7.35 | 40 | 8 to 15 |
| Before administration | 8.5 | >1.010 | +++ | 7.195 | 43.8 | 16.9 |
| 1st day | 7.0 | >1.030 | +++ | — | — | — |
| 4th day | 6.5 | >1.030 | +++ | — | — | — |
| 7th day | 6.5 | >1.030 | + | 7.136 | 36.3 | 12.2 |
| 10th day | 6.5 | >1.030 | +/− | — | — | — |
| 13th day | 6.5 | >1.030 | + | 7.129 | 33.9 | 11.2 |
| 17th day | 6.5 | >1.030 | +/− | — | — | — |
| 27th day | 6.0 | >1.030 | − | 7.166 | 38.2 | 13.8 |

As shown in Table 1, in the 4th day from the initial administration, the urine pH was decreased from 8.5 to 6.5 or less, and thereafter the blood pH was maintained stably within the normal range. Regarding the external appearance, the cat was spirited, the appetite was improved and the urine was smoothly excreted. After the administration for 27 days, no clinically abnormal remark was observed and the cat was maintained in good condition.

Although the administration of DL-methionine in a dose of 1 g/day per body usually affects the palatability adversely, said tablet has an improved palatability, and thus, can be supplied without any trouble, and decrease the urine pH with only a half dose as large as that of DL-methionine.

Administration of one tablet/body twice a day decreased the urinary pH more stably than that of administration of two tablets (0.5 g) per body simultaneously once a day.

Example 2

A tablet (0.5 g) containing 490 mg of fumaric acid per tablet was administered orally once a day for 74 days to a hybrid dog (male, 5-years-old, 3.5 kg of body weight) in which, as the results of the urine examination, bleeding in urine was observed, urination was hard and the urine pH was as high as 7.0, thus was diagnosed as struvite urinary calculosis. As a result, the palatability was not affected adversely and the administration was carried out with easy and simple manner. The measured values or evaluated characteristics, e.g. the urine pH, were determined or evaluated in the same manner as in Example 1, and the results shown in Table 2 were obtained.

pH of 7.5, were administered an antibiotic and 0.5 g of DL-methionine as a urine-acidifying agent for a nosotropic therapy. Immediately after the initial administration, the urine pH was reduced to 6.5, but owing to the poor palatability of the agent, the administration was unavoidable to be stopped. Accompanying with the interruption of the administration, the urine pH was elevated up to 7.5.

Thereafter, a feed prepared by adding 0.5% by weight of fumaric acid to a marketed wet food was supplied daily (200 to 300 mg/day/kg of body weight as fumaric acid), and in the 7th day from the initial administration, the urine pH was decreased to 6.0. The administration was continued for about consecutive 60 days thereafter in the same manner as above, and the urine pH in the 23th day, 31th day, 37th day and 61th day was at 6.5 respectively and the urine pH was maintained within the range of 6.0 to 6.5. Further, no clinical remark as abnormal was observed during this period.

Example 4

A prescribed diet (trade name: Hills C-S/D, manufactured by Hills Co., Ltd.) was fed for half a year to a cocker spaniel dog (female, 5-years-old, 12 kg of body weight) having a chronically increased urine pH, and the urine pH was maintained at about 6.0 during the feeding of said diet. The feeding was, however, ceased since the feeding for over half a year has a risk of causing metabolic acidosis and proteinous malnutrition. Immediately after the interruption of feeding of said prescribed diet, the urine pH raised up to 8.0–8.5 and the dog fell in dysuria. Further, DL-methionine

TABLE 2

|  | Urine pH | Specific gravity of urine | Protein in urine | Blood pH | Blood $pCO_2$ (mm Hg) | Blood $HCO_3^-$ (m mol/liter) |
| --- | --- | --- | --- | --- | --- | --- |
| Normal values | 7.0 or less | 1.018 to 1.045 | — | 7.10 to 7.35 | 40 | 8 to 15 |
| Before administration | 7.0 | 1.015 | +++ | — | — | — |
| 1st day | 7.0 | >1.025 | +++ | — | — | — |
| 12th day | 6.0 | >1.025 | ++ | — | — | — |
| 15th day | 6.0 | >1.015 | + | — | — | — |
| 25th day | 6.0 | >1.010 | − | — | — | — |
| 39th day | 6.0 | >1.010 | − | — | — | — |
| 48th day | 6.0 | >1.030 | − | 7.286 | 40.4 | 19.2 |
| 60th day | 5.0 | >1.010 | − | 7.381 | 29.0 | 17.2 |
| 68th day | 6.5 | >1.015 | − | — | — | — |
| 74th day | 6.5 | >1.010 | − | 7.166 | 38.2 | 13.8 |

It is apparent from Table 2 that, in the 12th day from the initial administration, the urine pH was lowered to 6.0 and the urination was improved to be normal. The evaluation of protein in urine was changed to "−", that is changed to negative in the 25th day from the initial administration and thereafter maintained as negative. As remarks of external appearance, the activity and appetite of the dog were increased.

Further, said tablet was administered in a dose of 0.5 g/day for 2.5 months thereafter. Consequently, the urine pH and blood pH were stabilized and a clinically irregular remark was not observed with regard to the respiration rate, body temperature, appetite and urination, and the conditions of the dog remained normal.

Example 3

To a Maltese dog (male, 5-years-old, 3.5 kg of body weight) which was diagnosed as urocystitis having a urine was tried to be supplied but the dog rejected to take any meal.

Subsequently, a feed added with 0.5% by weight of fumaric acid was administered twice a day (250 mg/day/kg of body weight as fumaric acid) after meal, and the urine pH was reduced to 7.5 after one week from the initial administration. The administration was continued till the 42th day after the initial administration, and the urine pH was maintained within the range of 6.5 to 7.0 and no abnormal or irregular remark was observed in vigor and appetite of the dog, with making satisfactory progress.

The administration of the feed added with 0.5% by weight of fumaric acid was stopped during the 48th day to 95th day from the initial administration, consequently, the urine pH was raised to 8.5.

Hence the administration of the feed added with 0.5% by weight of fumaric acid was reopened, and in the 13th day from the initial of the readministration, the urine pH was reduced to 6.5 and no perverted remark was clinically observed, with favorable progress. In the 18th day from the initial of the readministration, the urine pH and the blood pH were 6.5 and 7.362 respectively, and the blood $pCO_2$ (mm Hg) and the blood $HCO_3^-$ (m mol per liter) were 50.0 and 28.3 separately.

Example 5

To a melted mixture of 3 parts by weight of beeswax, 1 part by weight of paraffin wax and 31 parts by weight of hardened beef oil was added 65 parts by weight of fumaric acid for food additive (finer than 80 mesh, Takeda Chemical Industries, Ltd.) at about 80° to 100° C., and the mixture was granulated by spraying to provide a coated fumaric acid.

A marketed pet food (wet food) added with 0.5 g, per meal (110 g), of the coated fumaric acid thus obtained was fed twice a day, in the morning and in the evening, to a hybrid dog (male, 6-years-old, 7.0 kg of body weight) diagnosed as urinary calculosis in which the urine pH was 7.7, and in the 7th day from the initial feeding, the urine pH was decreased to 6.2. The palatability was not affected adversely and the feeding (administration) was carried out with ease and simplicity.

Preparation Example 1

To 98 parts by weight of fumaric acid usable as a food additive (32 to 200 mesh, Takeda Chemical Industries, Ltd.) was added 2 parts by weight of sucrose ester, and the mixture was compression-molded into a round form with a tablet machine (Hata Tekko, Co., Ltd., Japan) to provide 500 mg-tablets (size: 10 mmφ×5 mm) and 250 mg-tablets (size: 10 mmφ×2.5 mm).

Preparation Example 2

To 97 parts by weight of fumaric acid for a food additive (32 to 200 mesh, Takeda Chemical Industries, Ltd.) were added 2 parts by weight of sucrose ester and 1 part by weight of silicon dioxide (trade name: Carplex, Shionogi Pharmaceuticals, Ltd.), and the mixture was compression-molded into round form with a tablet machine (Hata Tekko Co., Ltd., Japan) to provide 250 mg-tablets (size: 10 mmφ×2.5 mm).

Preparation Example 3

Lactose (20 parts by weight) and crystalline cellulose (10 parts by weight) were added to 50 parts by weight of fumaric acid usable as a food additive (80 mesh pass, Takeda Chemical Industries, Ltd.), and the mixture was extrusion-granulated and dried to prepare granulated preparations (size: 0.5 mmφ×1 to 4 mm). To 80 parts by weight of said granulated preparations was sprayed gelatin for coating the surface of the granulated preparations to provide granules. The granules thus obtained were composed of 50% by weight of fumaric acid, 20% by weight of lactose, 10% by weight of crystalline cellulose and 20% by weight of gelatin.

Preparation Example 4

To 70 parts by weight of DL-malic acid for a food additive (a marketed product, manufactured by Fuso Chemical Industries, Ltd., Japan) were added 5 parts by weight of sucrose ester, 4 parts by weight of silicon dioxide, 1 part by weight of magnesium stearate and 20 part by weight of reducing maltose starch syrup, and the mixture was compressed and molded into round form with a tablet machine (Hata Tekko Co., Ltd., Japan) to provide 250-mg tablets (size: 10 mmφ×2.5 mm).

Preparation Example 5

To a melted mixture of 3 parts by weight of beeswax, 1 part by weight of paraffin wax and 31 parts by weight of hardened beef oil was added 65 parts by weight of fumaric acid for food additive (finer than 80 mesh, Takeda Chemical Industries, Ltd.) at about 80° to 100° C., and the mixture was granulated by spraying to prepare a coated fumaric acid.

To a mixture of 15 parts by weight of dry milled or pulverized fish meal (finer than 48 mesh), 15 parts by weight of dry meat-and-bone meal (finer than 48 mesh), 5 parts by weight of skimmed milk, 23 parts by weight of starch, 35 parts by weight of wheat flour, 3 parts by weight of sucrose ester, 2 parts by weight of animal oil, 1 part by weight of the total weight of vitamins and minerals, and 1 part by weight of the coated fumaric acid obtained above, was added 55 parts by weight of water, and blended or mixed. The resulting mixture was compressed and molded into cylindrical form with a disk-pellet granulating machine (Fuji Powdel Co., Ltd., Japan) to prepare 100 to 300 mg-pellets (size: 4 mmφ×about 5 to 10 mm). The pellet were dried at 50° C. for 10 hours to obtain a dry food. The dry food contained 9% by weight of water as determined by Karl Fischer's method.

What is claimed is:

1. A food as a therapeutic or prophylactic treatment for urinary calculosis in an animal consisting essentially of fumaric acid; having a mean particle size of not finer than 300 mesh and a base component selected from the group consisting of a feed of animal origin, a cereal, a starch, an oil meal, a bran, a cellulosic material, an excipient, a binder, a disintegrator, sodium chloride, sugar, an amino acid, and mixtures thereof, wherein said food includes not more than 1% vitamins and minerals based on the weight of the food.

2. A pet food according to claim 1, which is a dry food, a semidry food or a wet food.

3. A food according to claim 1 which comprises 0.01 to 10% by weight of said fumaric acid, based on the total weight of the food.

4. A food according to claim 1, wherein said fumaric acid is solid at room temperature.

5. A food according to claim 1, wherein said fumaric acid is in powdery or granular form and has a mean particle size of not finer than 300 mesh, and said fumaric acid is present in an amount from 0.05 to 5% by weight, based on the total weight of the food.

6. A food according to claim 5, which is a dry food, and said fumaric acid has a mean particle size of 200 to 10 mesh.

7. A method of treating or preventing urinary calculosis in an animal comprising administering to an animal in need of such treatment, an effective amount of food effective to treat urinary calculosis, said food consisting essentially of fumaric acid having a mean particle size of not finer than 300 mesh; and a base component selected from the group consisting of a feed of animal origin, a cereal, a starch, an oil meal, a bran, a cellulosic material, an excipient, a binder, a disintegrator, sodium chloride, sugar, an amino acid, and mixtures thereof, wherein said food includes not more than 1% vitamins and minerals based on the weight of the food.

8. A method of treating urinary calculosis in a animal according to claim 7, wherein said fumaric acid or a salt thereof is administered or fed to the pet in an amount of, in terms of the organic acid, 5 to 500 mg/day per kg of body weight.

9. A method of treating urinary calculosis in a animal according to claim 7, wherein said fumaric acid or a salt thereof is administered or fed to the pet as a preparation or a pet food in an effective amount to maintain the urine pH at 5.0 to 7.0.

10. A method of treating urinary calculosis in a animal according to claim 7, wherein fumaric acid or a salt thereof being solid at room temperature is administered or fed to the pet.

11. A method of treating urinary calculosis in a animal according to claim 10, wherein a preparation or a pet food comprising powdery or granular fumaric acid or a salt thereof having a mean grain or particle size of not finer than 300 mesh is administered or fed to the pet.

12. A method of treating urinary calculosis according to claim 7, wherein fumaric acid or a salt thereof is administered or fed to the animal in a plurality of times per day.

13. A food as recited in claim 1, wherein said fumaric acid is present in an amount from about 0.1 to 2.5% by weight.

14. A food as recited in claim 13, wherein said fumaric acid is present in an amount from about 0.1 to 1% by weight.

15. A food as recited in claim 1, wherein said base component is selected from the group consisting of a feed of animal origin, a cereal, a starch, an oil meal, a bran, a cellulosic material, a binder, sodium chloride, sugar, an amino acid, and mixtures thereof.

* * * * *